(12) United States Patent  (10) Patent No.: US 7,697,122 B2
Yamashita et al.  (45) Date of Patent: Apr. 13, 2010

(54) MEASURING DEVICE, METHOD, PROGRAM, AND RECORDING MEDIUM

(75) Inventors: Tomoyu Yamashita, Saitama (JP); Eiji Kato, Gunma (JP)

(73) Assignee: Advantest Corporation, Tokyo (JP)

( * ) Notice: Subject to any disclaimer, the term of this patent is extended or adjusted under 35 U.S.C. 154(b) by 0 days.

(21) Appl. No.: 12/065,658

(22) PCT Filed: Sep. 4, 2006

(86) PCT No.: PCT/JP2006/317924

§ 371 (c)(1),
(2), (4) Date: Apr. 17, 2008

(87) PCT Pub. No.: WO2007/029836

PCT Pub. Date: Mar. 15, 2007

(65) Prior Publication Data

US 2008/0231850 A1   Sep. 25, 2008

(30) Foreign Application Priority Data

Sep. 7, 2005 (JP) .............................. 2005-259244

(51) Int. Cl.
*G01N 21/00* (2006.01)
(52) U.S. Cl. ..................................... 356/73.1
(58) Field of Classification Search ........................ None
See application file for complete search history.

(56) References Cited

U.S. PATENT DOCUMENTS

| 5,062,703 | A | * | 11/1991 | Wong et al. ................. 356/73.1 |
| 5,150,248 | A | * | 9/1992 | Alfano et al. ................ 398/147 |
| 5,406,368 | A | * | 4/1995 | Horiuchi et al. ............ 356/73.1 |
| 5,828,058 | A | * | 10/1998 | Yamada .................. 250/227.14 |
| 6,493,074 | B1 | * | 12/2002 | Imamura et al. .......... 356/124.5 |
| 6,859,283 | B2 | * | 2/2005 | Arbore et al. ............... 356/477 |

(Continued)

FOREIGN PATENT DOCUMENTS

EP  1621902  2/2006

(Continued)

OTHER PUBLICATIONS

English language Abstract of JP 2004-317573.

*Primary Examiner*—Tarifur Chowdhury
*Assistant Examiner*—Gordon J Stock, Jr.
(74) *Attorney, Agent, or Firm*—Greenblum & Bernstein, P.L.C.

(57) ABSTRACT

A frequency resolution for measuring transmission characteristics of a device under test is increased. With a measuring device including a first terahertz light generator that generates incident light, a second terahertz light generator that generates reference light having an optical frequency $f_1-f_2-f_{IF}$ different from an optical frequency $f_1-f_2$ of the incident light by a constant difference frequency $f_{IF}$, a terahertz light detector which outputs an light detection signal having the difference frequency $f_{IF}$ based on response light obtained by making the incident light incident to an optical fiber and the reference light, and a network analyzer that receives the light detection signal, thereby measuring characteristics of the optical fiber, a spectrum of the incident light (terahertz light) incident to the optical fiber includes the carrier frequency $(f_1-f_2)$, but does not include sideband frequencies $(f_1-f_2 \pm f_{IF})$. It is thus possible to reduce the effective spectrum width of the incident light. As a result, the frequency resolution increases in the measurement of the transmission characteristics of the optical fiber.

8 Claims, 4 Drawing Sheets

U.S. PATENT DOCUMENTS

| | | |
|---|---|---|
| 6,873,405 B2 * | 3/2005 | Kido et al. .................. 356/121 |
| 6,980,288 B2 | 12/2005 | Kido et al. |
| 7,079,231 B2 | 7/2006 | Kido et al. |
| 7,239,396 B2 * | 7/2007 | Krause et al. ............... 356/477 |
| 2003/0142320 A1 * | 7/2003 | Mells ......................... 356/484 |
| 2004/0067056 A1 | 4/2004 | Kido et al. |
| 2004/0130725 A1 | 7/2004 | Kido et al. |
| 2006/0062574 A1 | 3/2006 | Kido et al. |

FOREIGN PATENT DOCUMENTS

| | | |
|---|---|---|
| JP | 2004-317573 | 11/2004 |
| WO | 02/082038 | 10/2002 |
| WO | 03/005002 | 1/2003 |

* cited by examiner

MEASURING DEVICE, METHOD, PROGRAM, AND RECORDING MEDIUM

TECHNICAL FIELD

The present invention relates to measurement of transmission characteristics in the terahertz region of a device under test.

BACKGROUND ART

There has conventionally been known measurement of transmission characteristics of a device under test in the terahertz region.

Figure 1:
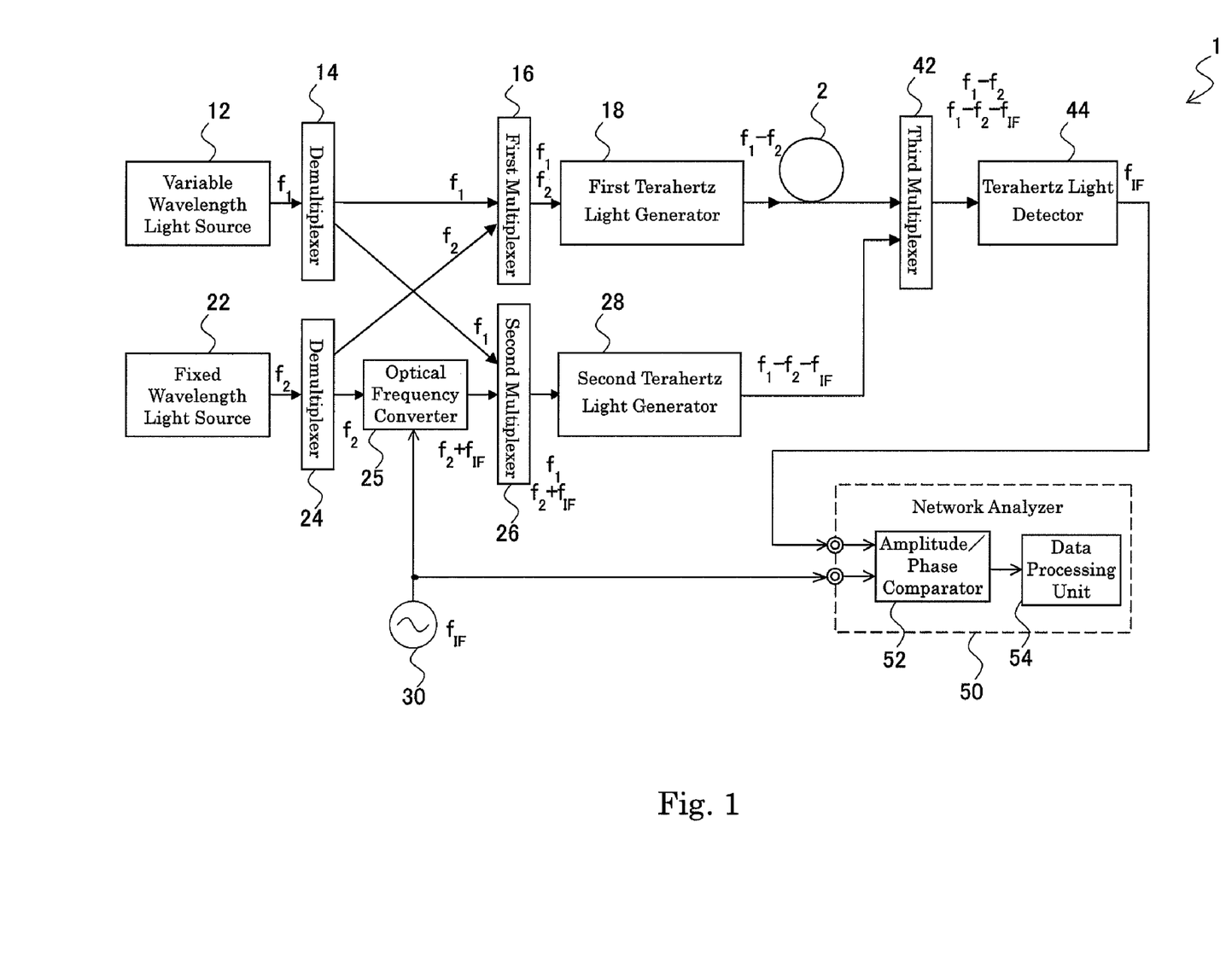
FIG. 1 is a functional block diagram showing a configuration of a measuring device 1 according a first embodiment.

For example, there has been known a device which measures transmission characteristics of a device under test using terahertz light modulated by an intensity modulation according to FIG. 1 of International Publication WO2003/005002. Terahertz light having a carrier frequency ($f_2-f_1$) and side band frequencies ($f_2-f_1 \pm f_{IF}$) is made incident to a device under test. As a result, the effective spectrum width (referred to as "incident spectrum width" hereinafter) of the terahertz light incident to the device under test becomes twice ($2 \times f_{IF}$) as wide as that of the modulation frequency $f_{IF}$.

However, according to the prior art described above, the frequency resolution of the transmission characteristics of the device under test decreases. The wider the incident spectrum width becomes, the lower the frequency resolution of the measurement of the transmission characteristics of the device under test becomes.

If the modulation frequency $f_{IF}$ is then decreased in order to increase the frequency resolution, the measurement accuracy for measuring the group delay time of the device under test (group delay resolution) decreases.

In this way, it is not possible for the prior art as described above to increase both the frequency resolution and the group delay resolution at the same time.

An object of the present invention is to increase the frequency resolution for measuring the transmission characteristics of a device under test.

DISCLOSURE OF THE INVENTION

According to an aspect of the present invention, a measuring device includes: an incident light generating unit that generates incident light; a reference light generating unit that generates reference light which has an optical frequency different from the optical frequency of the incident light by a constant difference frequency; a light detection signal output unit that outputs a light detection signal having the difference frequency based on response light obtained by making the incident light incident to a device under test and the reference light; and a characteristic measuring unit that receives the light detection signal, thereby measuring a characteristic of the device under test.

According to the thus constructed measuring device, an incident light generating unit generates incident light. A reference light generating unit generates reference light which has an optical frequency different from the optical frequency of the incident light by a constant difference frequency. A light detection signal output unit outputs a light detection signal having the difference frequency based on response light obtained by making the incident light incident to a device under test and the reference light. A characteristic measuring unit receives the light detection signal, thereby measuring a characteristic of the device under test.

According to the measuring device of the present invention, the response light may be light obtained by causing the incident light to transmit through the device under test.

According to the measuring device of the present invention, the response light may be light obtained by causing the incident light to be reflected by the device under test.

According to the present invention, the measuring device may include a difference frequency signal output unit that outputs a difference frequency signal having the difference frequency, wherein: the incident light generating unit includes: a variable wavelength light source that generates variable wavelength light; a fixed wavelength light source that generates fixed wavelength light; a first multiplexing unit that multiplexes the variable wavelength light and the fixed wavelength light with each other; and a first light output unit that receives an output from the first multiplexing unit, and outputs the incident light which has an optical frequency corresponding to a difference between the optical frequency of the variable wavelength light and the optical frequency of the fixed wavelength light, and the reference light generating unit includes: the variable wavelength light source; the fixed wavelength light source; an optical frequency converting unit that receives the difference frequency signal and the fixed wavelength light, and converts the optical frequency of the fixed wavelength light by the amount of the difference frequency; a second multiplexing unit that multiplexes the variable wavelength light and an output from the optical frequency converting unit with each other; and a second light output unit that receives an output from the second multiplexing unit, and outputs the reference light.

According to the measuring device of the present invention, the characteristic measuring unit may receive the difference frequency signal and the light detection signal, and measure the characteristic of the device under test.

According to the present invention, the measuring device may include: a base multiplexing unit that multiplexes the incident light and the reference light with each other; and a reference signal output unit that receives an output from the base multiplexing unit, and outputs a reference signal having the difference frequency, wherein the characteristic measuring unit receives the reference signal and the light detection signal, and measures the characteristic of the device under test.

According to another aspect of the present invention, a measuring method includes: an incident light generating step of generating incident light; a reference light generating step of generating reference light which has an optical frequency different from the optical frequency of the incident light by a constant difference frequency; a light detection signal output step of outputting a light detection signal having the difference frequency based on response light obtained by making the incident light incident to a device under test and the reference light; and a characteristic measuring step of receiving the light detection signal, thereby measuring a characteristic of the device under test.

Another aspect of the present invention is a program of instructions for execution by the computer to perform a process of a measuring device having: an incident light generating unit that generates incident light; a reference light generating unit that generates reference light which has an optical frequency different from the optical frequency of the incident light by a constant difference frequency; and a light detection signal output unit that outputs a light detection signal having the difference frequency based on response light obtained by making the incident light incident to a device under test and the reference light, the process including: a characteristic measuring step of receiving the light detection signal, thereby measuring a characteristic of the device under test.

Another aspect of the present invention is a computer-readable medium having a program of instructions for execution by the computer to perform a process of a measuring device having: an incident light generating unit that generates incident light; a reference light generating unit that generates reference light which has an optical frequency different from the optical frequency of the incident light by a constant difference frequency; and a light detection signal output unit that outputs a light detection signal having the difference frequency based on response light obtained by making the incident light incident to a device under test and the reference light, the process including: a characteristic measuring step of receiving the light detection signal, thereby measuring a characteristic of the device under test.

BEST MODE FOR CARRYING OUT THE INVENTION

A description will now be given of an embodiment of the present invention with reference to drawings.

First Embodiment

FIG. 1 is a functional block diagram showing a configuration of a measuring device 1 according a first embodiment. The measuring device 1 according to the first embodiment is a device for measuring transmission characteristics (such as an amplitude characteristic and a phase characteristic) of an optical fiber (device under test) 2. The measuring device 1 includes a variable wavelength light source 12, a demultiplexer 14, a first multiplexer 16, a first terahertz light generator (first light output means) 18, a fixed wavelength light source 22, a demultiplexer 24, an optical frequency converter 25, a second multiplexer 26, a second terahertz light generator (second light output means) 28, a difference frequency signal source 30, a third multiplexer 42, a terahertz light detector (light detection signal output means) 44, and a network analyzer (characteristic measuring means) 50.

The variable wavelength light source 12 generates variable wavelength light. The variable wavelength light is continuous wave (CW) light with an optical frequency $f_1$. The optical frequency $f_1$ of the variable wavelength light changes from $f_2+\Delta f_{low}$ to $f_2+\Delta f_{high}$.

The demultiplexer 14 receives the variable wavelength light from the variable wavelength light source 12, demultiplexes the variable wavelength light, and outputs the demultiplexed light to the first multiplexer 16 and the second multiplexer 26.

The fixed wavelength light source 22 generates fixed wavelength light. The fixed wavelength light is CW light with an optical frequency $f_2$. The optical frequency $f_2$ of the fixed wavelength light is constant.

The demultiplexer 24 receives the fixed wavelength light from the fixed wavelength light source 22, demultiplexes the fixed wavelength light, and outputs the demultiplexed light to the first multiplexer 16 and the optical frequency converter 25.

The difference frequency signal source 30 outputs a difference frequency signal having a difference frequency $f_{IF}$.

The optical frequency converter 25 receives the difference frequency signal from the difference frequency signal source 30, and further receives the fixed wavelength light from the fixed wavelength light source 22. The optical frequency converter 25 then converts the optical frequency $f_2$ of the fixed wavelength light by the amount of the difference frequency $f_{IF}$, and outputs the converted light. Though the optical frequency of the output from the optical frequency converter 25 may be $f_2+f_{IF}$ or $f_2-f_{IF}$, it is assumed that the optical frequency of the output from the optical frequency converter 25 is $f_2+f_{IF}$ according to the present embodiment. The light output by the optical frequency converter 25 is fed to the second multiplexer 26.

The first multiplexer 16 receives the variable wavelength light from the demultiplexer 14, and further receives the fixed wavelength light from the demultiplexer 24. The first multiplexer 16 then multiplexes the variable wavelength light and the fixed wavelength light with each other.

The first terahertz light generator (first light output means) 18 receives an output from the first multiplexer 16, and outputs incident light having an optical frequency $f_1-f_2$, which is a difference between the optical frequency $f_1$ of the variable wavelength light and the optical frequency $f_2$ of the fixed wavelength light.

The first terahertz light generator 18 can be constituted by forming parallel transmission paths on a light conducting film made of low-temperature-growth gallium arsenide, for example. The incident light is terahertz light (optical frequency thereof is 0.1 THz to 10 THz).

The incident light is made incident to one end of the optical fiber (device under test) 2. The incident light transmits through the optical fiber 2, and emerges from the other end of the optical fiber 2. The light obtained from the optical fiber 2 as a result of the incident light made incident to the optical fiber 2 in this way is referred to as response light. The response light is light obtained by causing the incident light to transmit through the optical fiber 2 according to the first embodiment.

The second multiplexer 26 receives the variable wavelength light from the demultiplexer 14, and further receives the light output by the optical frequency converter 25. The second multiplexer 26 then multiplexes the variable wavelength light and the light output by the optical frequency converter 25 with each other.

The second terahertz light generator (second light output means) 28 receives an output from the second multiplexer 26, and outputs light having an optical frequency $f_1-f_2-f_{IF}$, which is a difference between the optical frequency $f_1$ of the variable wavelength light and the optical frequency $f_2+f_{IF}$ of the light output by the optical frequency converter 25. The second terahertz light generator 28 can be constituted by forming parallel transmission paths on a light conducting film made of low-temperature-growth gallium arsenide, for example. The light output by the second terahertz light generator 28 is referred to as reference light. The optical frequency of the reference light is $f_1-f_2-f_{IF}$, and is different in frequency from the optical frequency $f_1-f_2$ of the incident light by the constant difference frequency $f_{IF}$. Moreover, the reference light is terahertz light (optical frequency thereof is 0.1 THz to 10 THz).

It should be noted that the variable wavelength light source 12, the demultiplexer 14, the first multiplexer 16, the first terahertz light generator 18, the fixed wavelength light source 22, and the demultiplexer 24 correspond to incident light generating means which generates the incident light. Moreover, the variable wavelength light source 12, the demultiplexer 14, the fixed wavelength light source 22, the demultiplexer 24, the optical frequency converter 25, the second multiplexer 26, and the second terahertz light generator 28 correspond to reference light generating means which generates the reference light.

The third multiplexer 42 receives the response light from the optical fiber 2. Moreover, the third multiplexer 42 receives the reference light from the second terahertz light generator 28. The third multiplexer 42 then multiplexes the response light and the reference light with each other, and feeds the multiplexed light to the terahertz light detector 44.

The terahertz light detector (light detection signal output means) 44 receives the output by the third multiplexer 42, and outputs a light detection signal having the frequency $f_{IF}$ (namely, the difference frequency $f_{IF}$) which is a difference between the optical frequency $f_1-f_2$ of the response light and the optical frequency $f_1-f_2-f_{IF}$ of the reference light. In other words, the terahertz light detector 44 outputs the optical detection signal based on the response light and the reference light. It should be noted the terahertz light detector 44 may have a configuration as that of the first terahertz light generator 18 and the second terahertz light generator 28.

The network analyzer (characteristic measuring means) 50 receives the light detection signal from the terahertz light detector 44. Moreover, the network analyzer 50 receives the difference frequency signal which has the difference frequency $f_{IF}$ from the difference frequency signal source 30. The network analyzer 50 measures characteristics of the optical fiber 2 based on the light detection signal and the difference frequency signal. The network analyzer 50 measures transmission characteristics (such as amplitude characteristic and phase characteristic) of the optical fiber 2, for example.

The network analyzer 50 includes an amplitude/phase comparator 52 and a data processing unit 54. The amplitude/phase comparator 52 compares the amplitude of the light detection signal and the amplitude of the difference frequency signal with each other. The amplitude/phase comparator 52 divides the amplitude of the light detection signal by the amplitude of the difference frequency signal, for example. Moreover, the amplitude/phase comparator 52 compares the phase of the light detection signal and the phase of the difference frequency signal with each other. The amplitude/phase comparator 52 subtracts the phase of the difference frequency signal from the phase of the light detection signal, for example.

The data processing unit 54 derives the transmission characteristics of the optical fiber 2 based on a result of the comparisons on the amplitude/phase comparator 52. It is possible to measure the amplitude and the phase of the response light obtained by causing the incident light (terahertz light) having the optical frequency $f_1-f_2$ to transmit through the optical fiber 2. Moreover, the optical frequency $f_1$ of the variable wavelength light changes from $f_2+\Delta f_{low}$ to $f_2+\Delta f_{high}$. As a result, the amplitude characteristic and the phase characteristic of the optical fiber 2 are measured in the range of the optical frequency of the incident light from $\Delta f_{low}$ to $\Delta f_{high}$.

A description will now be given of an operation of the first embodiment.

First, the variable wavelength light source 12 generates the variable wavelength light (optical frequency $f_1$), and the fixed wavelength light source 22 generates the fixed wavelength light (optical frequency $f_2$). It should be noted that the optical frequency $f_1$ changes from $f_2+\Delta f_{low}$ to $f_2+\Delta f_{high}$.

The demultiplexer 14 then receives the variable wavelength light from the variable wavelength light source 12, demultiplexes the variable wavelength light, and outputs the demultiplexed light to the first multiplexer 16 and the second multiplexer 26. Moreover, the demultiplexer 24 receives the fixed wavelength light from the fixed wavelength light source 22, demultiplexes the fixed wavelength light, and outputs the demultiplexed light to the first multiplexer 16 and the optical frequency converter 25. It should be noted that the difference frequency signal having the difference frequency $f_{IF}$ is also fed from the difference frequency signal source 30 to the optical frequency converter 25.

The first multiplexer 16 multiplexes the variable wavelength light and the fixed wavelength light with each other. The first terahertz light generator 18 receives the output from the first multiplexer 16, and outputs the incident light having the optical frequency $f_1-f_2$, which is the difference between the optical frequency $f_1$ of the variable wavelength light and the optical frequency $f_2$ of the fixed wavelength light.

The incident light is made incident to the one end of the optical fiber 2. The incident light transmits through the optical fiber 2, and emerges as the response light from the other end of the optical fiber 2. The response light is fed to the third multiplexer 42.

The optical frequency converter 25 converts the optical frequency $f_2$ of the fixed wavelength light by the amount of the difference frequency $f_{IF}$, and outputs the converted light. The light (optical frequency $f_2+f_{IF}$) output by the optical frequency converter 25 is fed to the second multiplexer 26.

The second multiplexer 26 multiplexes the variable wavelength light and the light output by the optical frequency converter 25 with each other. The second terahertz light generator (second light output means) 28 receives the output from the second multiplexer 26, and outputs the reference light having the optical frequency $f_1-f_2-f_{IF}$, which is the difference between the optical frequency $f_1$ of the variable wavelength light and the optical frequency $f_2+f_{IF}$ of the light output by the optical frequency converter 25. The reference light is fed to the third multiplexer 42.

The third multiplexer 42 multiplexes the response light and the reference light with each other, and feeds the multiplexed light to the terahertz light detector 44. The terahertz light detector 44 receives the output from the third multiplexer 42, and outputs the light detection signal having the frequency $f_{IF}$ (namely, the difference frequency $f_{IF}$) which is the difference between the optical frequency $f_1-f_2$ of the response light and the optical frequency $f_1-f_2-f_{IF}$ of the reference light.

The network analyzer 50 receives the light detection signal and the difference frequency signal, and measures the characteristics of the optical fiber 2. Specifically, the amplitude/phase comparator 52 compares the amplitude (phase) of the light detection signal and the amplitude (phase) of the difference frequency signal with each other. The data processing unit 54 carries out the data processing based on the result of the comparison, thereby measuring the amplitude characteristic and the phase characteristic of the optical fiber 2 within the range of the optical frequency of the incident light from $\Delta f_{low}$ to $\Delta f_{high}$.

According to the first embodiment, the spectrum of the incident light (terahertz light) incident to the optical fiber 2 includes the carrier frequency $(f_2-f_1)$, but does not include side band frequencies $(f_1-f_2 \pm f_{IF})$. It is thus possible to reduce the effective spectrum width of the incident light. As a result, the frequency resolution increases in the measurement of the transmission characteristics of the optical fiber 2. It should be noted that the frequency resolution is a high value determined by the optical frequency stability of the variable wavelength light source 12 and the fixed wavelength light source 22.

Moreover, the response light acquired from the optical fiber 2 is not detected by a direct detection, but by a heterodyne detection of the terahertz optical detector 44 according to the first embodiment, and the measurement with a wide dynamic range and a high sensitivity can thus be provided.

Further, according to the first embodiment, the incident light and the reference light are generated by the variable wavelength light source 12 and the fixed wavelength light source 22. It is assumed that the optical frequency $f_1$ of the variable wavelength light and the optical frequency $f_2$ of the fixed wavelength light are unstable, and thus change respectively to $f_1'$ and $f_2'$ on this occasion. However, the frequency of the light detection signal output by the terahertz light detector 44 is still the difference frequency $f_{IF}$. As a result, even if the optical frequency $f_1$ of the variable wavelength light and the optical frequency $f_2$ of the fixed wavelength light are unstable, the heterodyne detection by the terahertz light detector 44 cancels out the instability thereof, resulting in a stable measurement.

Second Embodiment

Figure 2:
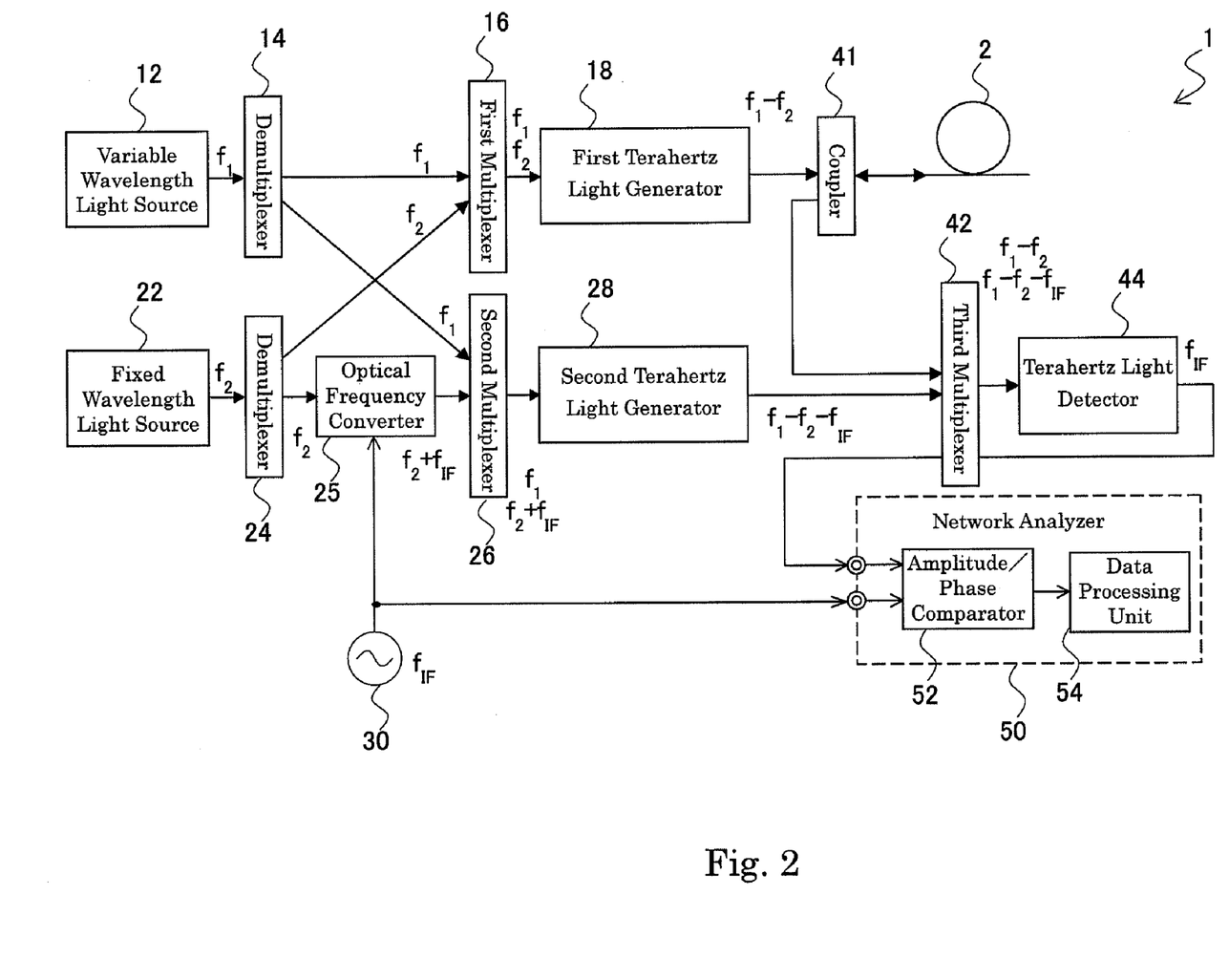
FIG. 2 is a functional block diagram showing a configuration of a measuring device 1 according a second embodiment.

A second embodiment is different from the first embodiment in that the response light is reflected light by the optical fiber 2.

FIG. 2 is a functional block diagram showing a configuration of the measuring device 1 according the second embodiment. The measuring device 1 according to the second embodiment includes the variable wavelength light source 12, the demultiplexer 14, the first multiplexer 16, the first terahertz light generator (first light output means) 18, the fixed wavelength light source 22, the demultiplexer 24, the optical frequency converter 25, the second multiplexer 26, the second terahertz light generator (second light output means) 28, the difference frequency signal source 30, a coupler 41, the third multiplexer 42, the terahertz light detector (light detection signal output means) 44, and the network analyzer (characteristic measuring means) 50. In the following section, like components are denoted by like numerals as of the first embodiment, and will be explained in no more details.

The coupler 41 is connected to the first terahertz light generator 18, the optical fiber 2, and the third multiplexer 42. The coupler 41 feeds the incident light output by the first terahertz light generator 18 to the one end of the optical fiber 2. Moreover, the coupler 41 feeds light which has been reflected by the optical fiber 2, and has returned to the one end of the optical fiber 2, to the third multiplexer 42.

The components other than the coupler 41 are the same as those in the first embodiment, and a description thereof, therefore, is omitted. It should be noted that the incident light output by the first terahertz light generator 18 is made incident to the one end of the optical fiber 2 via the coupler 41. The response light is light obtained by causing the incident light to be reflected by the optical fiber 2. The third multiplexer 42 receives the response light from the optical fiber 2 via the coupler 41.

A description will now be given of an operation of the second embodiment.

First, the variable wavelength light source 12 generates the variable wavelength light (optical frequency $f_1$), and the fixed wavelength light source 22 generates the fixed wavelength light (optical frequency $f_2$). It should be noted that the optical frequency $f_1$ changes from $f_2+\Delta f_{low}$ to $f_2+\Delta f_{high}$.

The demultiplexer 14 then receives the variable wavelength light from the variable wavelength light source 12, demultiplexes the variable wavelength light, and outputs the demultiplexed light to the first multiplexer 16 and the second multiplexer 26. Moreover, the demultiplexer 24 receives the fixed wavelength light from the fixed wavelength light source 22, demultiplexes the fixed wavelength light, and outputs the demultiplexed light to the first multiplexer 16 and the optical frequency converter 25. It should be noted that the difference frequency signal having the difference frequency $f_{IF}$ is also fed from the difference frequency signal source 30 to the optical frequency converter 25.

The first multiplexer 16 multiplexes the variable wavelength light and the fixed wavelength light with each other. The first terahertz light generator 18 receives the output from the first multiplexer 16, and outputs the incident light having the optical frequency $f_1-f_2$, which is the difference between the optical frequency $f_1$ of the variable wavelength light and the optical frequency $f_2$ of the fixed wavelength light.

The incident light is made incident to the one end of the optical fiber 2 via the coupler 41. The incident light is reflected by the optical fiber 2, returns to the one end of the optical fiber 2, and emerges from the one end of the optical fiber 2 as the response light. The response light is fed to the third multiplexer 42 via the coupler 41.

The optical frequency converter 25 converts the optical frequency $f_2$ of the fixed wavelength light by the amount of the difference frequency $f_{IF}$, and outputs the converted light. The light (optical frequency $f_2+f_{IF}$) output by the optical frequency converter 25 is fed to the second multiplexer 26.

The second multiplexer 26 multiplexes the variable wavelength light and the light output by the optical frequency converter 25 with each other. The second terahertz light generator (second light output means) 28 receives the output from the second multiplexer 26, and outputs reference light having the optical frequency $f_1-f_2-f_{IF}$, which is the difference between the optical frequency $f_1$ of the variable wavelength light and the optical frequency $f_2+f_{IF}$ of the light output by the optical frequency converter 25. The reference light is fed to the third multiplexer 42.

The third multiplexer 42 multiplexes the response light and the reference light with each other, and feeds the multiplexed light to the terahertz light detector 44. The terahertz light detector 44 receives the output from the third multiplexer 42, and outputs a light detection signal having the frequency $f_{IF}$ (namely, the difference frequency $f_{IF}$) which is the difference between the optical frequency $f_1-f_2$ of the response light and the optical frequency $f_1-f_2-f_{IF}$ of the reference light.

The network analyzer 50 receives the light detection signal and the difference frequency signal, and measures the characteristics of the optical fiber 2. Specifically, the amplitude/phase comparator 52 compares the amplitude (phase) of the light detection signal and the amplitude (phase) of the difference frequency signal with each other. The data processing unit 54 carries out the data processing based on the result of the comparison, thereby measuring the amplitude characteristic and the phase characteristic of the optical fiber 2 within the range of the optical frequency of the incident light from $\Delta f_{low}$ to $\Delta f_{high}$.

According to the second embodiment, there are obtained the same effects as in the first embodiment. Moreover, according to the second embodiment, the transmission characteristics of the optical fiber 2 can be measured based on the reflected light of the optical fiber 2.

Third Embodiment

Figure 3:
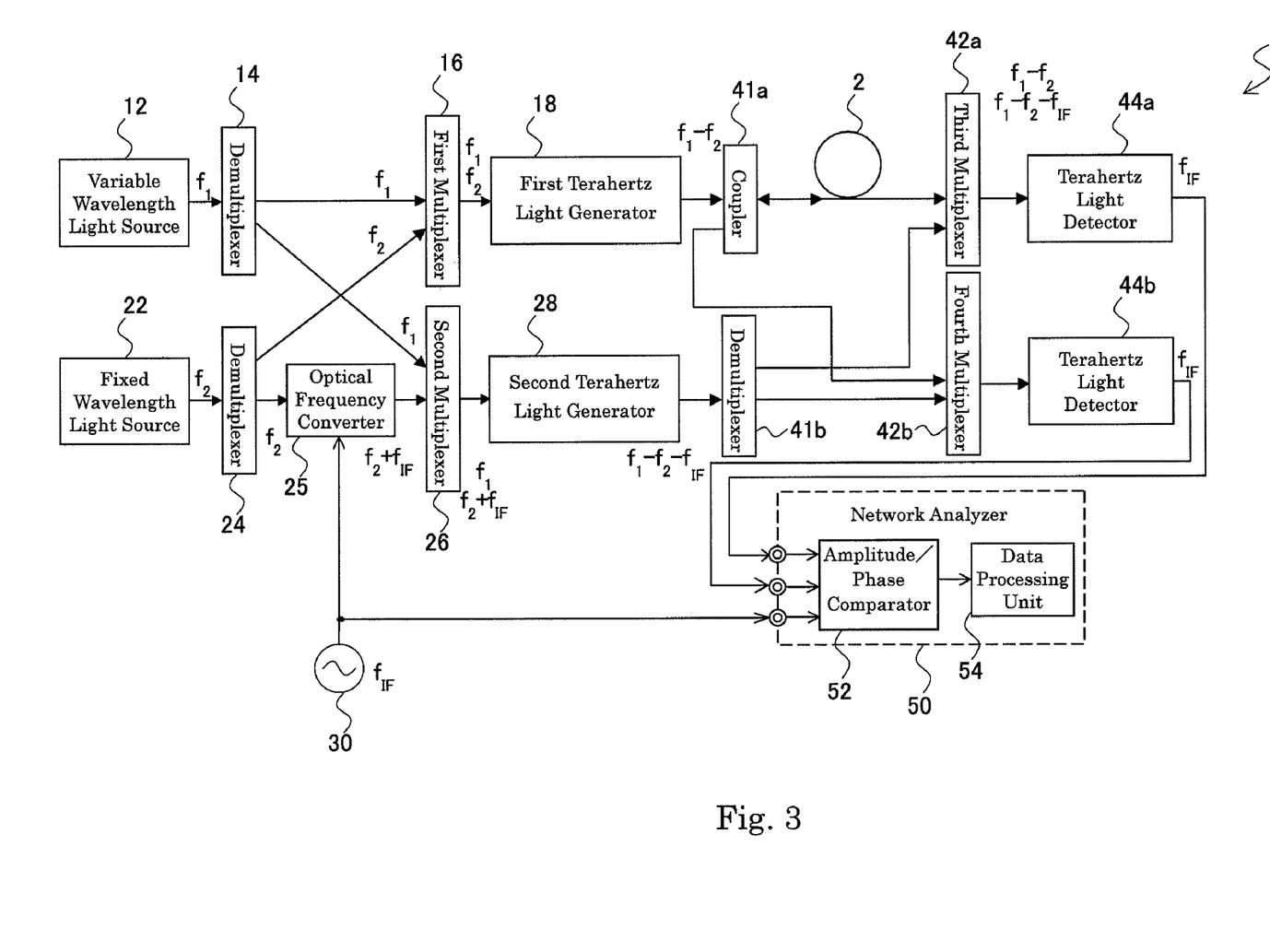
FIG. 3 is a functional block diagram showing a configuration of a measuring device 1 according a third embodiment.

A third embodiment is different from the first embodiment in that both the light which has transmitted through the optical fiber 2, and the light which has reflected by the optical fiber 2 are used as the response light.

FIG. 3 is a functional block diagram showing a configuration of the measuring device 1 according the third embodiment. The measuring device 1 according to the third embodiment includes the variable wavelength light source 12, the demultiplexer 14, the first multiplexer 16, the first terahertz light generator (first light output means) 18, the fixed wavelength light source 22, the demultiplexer 24, the optical frequency converter 25, the second multiplexer 26, the second terahertz light generator (second light output means) 28, the difference frequency signal source 30, a coupler 41a, a demultiplexer 41b, a third multiplexer 42a, a fourth multiplexer 42b, a terahertz light detector (light detection signal output means) 44a, a terahertz light detector (light detection signal output means) 44b, and the network analyzer (characteristic measuring means) 50. In the following section, like components are denoted by like numerals as of the first embodiment, and will be explained in no more details.

The coupler 41a is connected to the first terahertz light generator 18, the optical fiber 2, and the fourth multiplexer 42b. The coupler 41a feeds the incident light output by the first terahertz light generator 18 to the one end of the optical fiber 2. Moreover, the coupler 41 feeds light which has been reflected by the optical fiber 2, and has returned to the one end of the optical fiber 2 to the fourth multiplexer 42b.

The demultiplexer 41b demultiplexes the reference light output by the second terahertz light generator 28, and feeds the demultiplexed light to the third multiplexer 42a and the fourth multiplexer 42b.

The third multiplexer 42a receives first response light (light which has transmitted through the optical fiber 2) from the optical fiber 2. Moreover, the third multiplexer 42 receives the reference light from the demultiplexer 41b. The third multiplexer 42 then multiplexes the first response light and the reference light with each other, and feeds the multiplexed light to the terahertz light detector 44a.

The fourth multiplexer 42b receives second response light (light which has reflected by the optical fiber 2) from the optical fiber 2 via the coupler 41a. Moreover, the third multiplexer 42 receives the reference light from the demultiplexer 41b. The fourth multiplexer 42b then multiplexes the second response light and the reference light with each other, and feeds the multiplexed light to the terahertz light detector 44b.

The terahertz light detector (light detection signal output means) 44a and the terahertz light detector (light detection signal output means) 44b are the same as the terahertz light detector (light detection signal output means) 44 according to the first embodiment.

It should be noted that the terahertz light detector (light detection signal output means) 44a outputs a light detection signal having the frequency $f_{IF}$ (namely, the difference frequency $f_{IF}$) which is the difference between the optical frequency $f_1-f_2$ of the first response light and the optical frequency $f_1-f_2-f_{IF}$ of the reference light to the network analyzer 50.

On the other hand, the terahertz light detector (light detection signal output means) 44b outputs a light detection signal having the frequency $f_{IF}$ (namely, the difference frequency $f_{IF}$) which is the difference between the optical frequency $f_1-f_2$ of the second response light and the optical frequency $f_1-f_2-f_{IF}$ of the reference light to the network analyzer 50.

The components other than the coupler 41a, the demultiplexer 41b, the third multiplexer 42a, the fourth multiplexer 42b, the terahertz light detector (light detection signal output means) 44a, and the terahertz light detector (light detection signal output means) 44b are the same as those in the first embodiment, and a description thereof, therefore, is omitted. It should be noted that the incident light which has transmitted through the optical fiber 2 (first response light) and the incident light reflected by the optical fiber 2 (second response light) are used as the response light.

A description will now be given of an operation of the third embodiment.

First, the variable wavelength light source 12 generates the variable wavelength light (optical frequency $f_1$), and the fixed wavelength light source 22 generates the fixed wavelength light (optical frequency $f_2$). It should be noted that the optical frequency $f_1$ changes from $f_2+\Delta f_{low}$ to $f_2+\Delta f_{high}$.

The demultiplexer 14 then receives the variable wavelength light from the variable wavelength light source 12, demultiplexes the variable wavelength light, and outputs the demultiplexed light to the first multiplexer 16 and the second multiplexer 26. Moreover, the demultiplexer 24 receives the fixed wavelength light from the fixed wavelength light source 22, demultiplexes the fixed wavelength light, and outputs the demultiplexed light to the first multiplexer 16 and the optical frequency converter 25. It should be noted that the difference frequency signal having the difference frequency $f_{IF}$ is also fed from the difference frequency signal source 30 to the optical frequency converter 25.

The first multiplexer 16 multiplexes the variable wavelength light and the fixed wavelength light with each other. The first terahertz light generator 18 receives the output from the first multiplexer 16, and outputs the incident light having the optical frequency $f_1-f_2$, which is the difference between the optical frequency $f_1$ of the variable wavelength light and the optical frequency $f_2$ of the fixed wavelength light.

The incident light is made incident to the one end of the optical fiber 2 via the coupler 41a. The incident light transmits through the optical fiber 2, and emerges from the other end of the optical fiber 2 as the response light. The first response light (light which has transmitted through the optical fiber 2) is fed to the third multiplexer 42a.

The incident light is reflected by the optical fiber 2, returns to the one end of the optical fiber 2, and emerges as the second response light (light which has reflected by the optical fiber 2) from the one end of the optical fiber 2. The second response light is fed to the fourth multiplexer 42b via the coupler 41a.

The optical frequency converter 25 converts the optical frequency $f_2$ of the fixed wavelength light by the amount of the difference frequency $f_{IF}$, and outputs the converted light. The light (optical frequency $f_2+f_{IF}$) output by the optical frequency converter 25 is fed to the second multiplexer 26.

The second multiplexer 26 multiplexes the variable wavelength light and the light output by the optical frequency converter 25 with each other. The second terahertz light generator (second light output means) 28 receives the output from the second multiplexer 26, and outputs the reference light having the optical frequency $f_1-f_2-f_{IF}$, which is the difference between the optical frequency $f_1$ of the variable wavelength light and the optical frequency $f_2+f_{IF}$ of the light output by the optical frequency converter 25. The reference light is fed to the demultiplexer 41b. The demultiplexer 41b demultiplexes the reference light, and feeds the demultiplexed light to the third multiplexer 42a and the fourth multiplexer 42b.

The third multiplexer 42a multiplexes the first response light and the reference light with each other, and feeds the multiplexed light to the terahertz light detector 44a. The terahertz light detector 44a receives the output from the third multiplexer 42a, and outputs the light detection signal having the frequency $f_{IF}$ (namely, the difference frequency $f_{IF}$) which is the difference between the optical frequency $f_1-f_2$ of the first response light and the optical frequency $f_1-f_2-f_{IF}$ of the reference light.

The fourth multiplexer 42b multiplexes the second response light and the reference light with each other, and feeds the multiplexed light to the terahertz light detector 44b. The terahertz light detector 44b receives the output from the fourth multiplexer 42b, and outputs the light detection signal having the frequency $f_{IF}$ (namely, the difference frequency $f_{IF}$) which is the difference between the optical frequency $f_1-f_2$ of the second response light and the optical frequency $f_1-f_2-f_{IF}$ of the reference light.

The network analyzer 50 receives the light detection signals and the difference frequency signal, and measures the characteristics of the optical fiber 2. Specifically, the amplitude/phase comparator 52 compares the amplitude (phase) of the light detection signals and the amplitude (phase) of the difference frequency signal with each other. The data processing unit 54 carries out the data processing based on the result of the comparison, thereby measuring the amplitude characteristic and the phase characteristic of the optical fiber 2 within the range of the optical frequency of the incident light from $\Delta f_{low}$ to $\Delta f_{high}$.

According to the third embodiment, there are obtained the same effects as in the first embodiment. Moreover, it is possible to measure the transmission characteristics of the optical fiber 2 based on the transmitted light (first response light) which has transmitted through the optical fiber 2, and the reflected light (second response light) which has been reflected by the optical fiber 2 according to the third embodiment.

Fourth Embodiment

Figure 4:
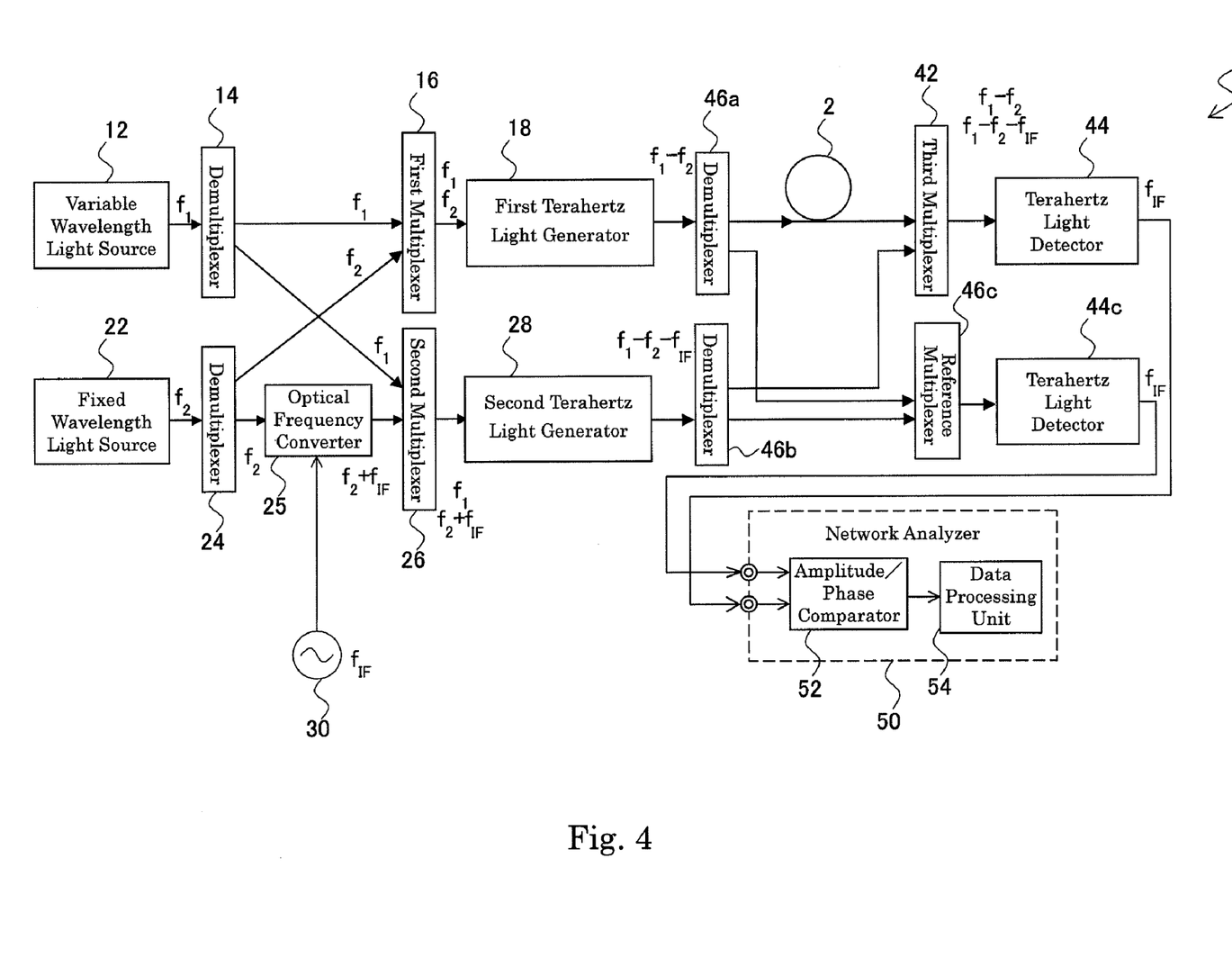
FIG. 4 is a functional block diagram showing a configuration of a measuring device 1 according a fourth embodiment.

A fourth embodiment is different from the first embodiment in that, in place of the difference frequency signal, a reference signal, which is obtained by multiplexing the incident light and the reference light with each other, and then detecting the multiplexed light by heterodyne detection on a terahertz optical detector 44c, is fed to the network analyzer 50.

FIG. 4 is a functional block diagram showing a configuration of the measuring device 1 according the fourth embodiment. The measuring device 1 according to the fourth embodiment includes the variable wavelength light source 12, the demultiplexer 14, the first multiplexer 16, the first terahertz light generator (first light output means) 18, the fixed wavelength light source 22, the demultiplexer 24, the optical frequency converter 25, the second multiplexer 26, the second terahertz light generator (second light output means) 28, the difference frequency signal source 30, the third multiplexer 42, the terahertz light detector (light detection signal output means) 44, the terahertz light detector (reference signal output means) 44c, a demultiplexer 46a, a demultiplexer 46b, a reference multiplexer 46c, and the network analyzer (characteristic measuring means) 50. In the following section, like components are denoted by like numerals as of the first embodiment, and will be explained in no more details.

The demultiplexer 46a receives the incident light from the first terahertz light generator 18, demultiplexes the incident light, and outputs the demultiplexed light to the optical fiber 2 and the reference multiplexer 46c.

The demultiplexer 46b demultiplexes the reference light output from the second terahertz light generator 28, and feeds the demultiplexed light to the third multiplexer 42 and the reference multiplexer 46c.

It should be noted that the third multiplexer 42 multiplexes the response light and the reference light with each other, and feeds the multiplexed light to the terahertz light detector 44 as in the first embodiment. However, the third multiplexer 42 receives the reference light from the second terahertz light generator 28 via the demultiplexer 46b.

The reference multiplexer 46c receives the incident light from the demultiplexer 46a. Moreover, the reference multiplexer 46c receives the reference light from the demultiplexer 46b. The reference multiplexer 46c then multiplexes the incident light and the reference light with each other, and feeds the multiplexed light to the terahertz light detector 44c.

The terahertz light detector (reference signal output means) 44c receives the output from the reference multiplexer 46c, and outputs the reference signal having the frequency $f_{IF}$ (namely, the difference frequency $f_{IF}$) which is the difference between the optical frequency $f_1-f_2$ of the incident light and the optical frequency $f_1-f_2-f_{IF}$ of the reference light.

The network analyzer (characteristic measuring means) 50 receives a light detection signal from the terahertz light detector 44, and the reference signal from the terahertz light detector 44c, thereby measuring the characteristics of the optical fiber 2. The network analyzer 50 includes the amplitude/phase comparator 52 and the data processing unit 54. The amplitude/phase comparator 52 compares the amplitude (phase) of the light detection signal and the amplitude (phase) of the reference signal with each other. The data processing unit 54 derives the transmission characteristics of the optical fiber 2 based on a result of the comparisons on the amplitude/phase comparator 52.

The components other than the demultiplexer 46a, the demultiplexer 46b, the reference multiplexer 46c, the terahertz light detector 44c, and the network analyzer 50 are the same as those in the first embodiment, and a description thereof, therefore, is omitted.

A description will now be given of an operation of the fourth embodiment.

First, the variable wavelength light source 12 generates the variable wavelength light (optical frequency $f_1$), and the fixed wavelength light source 22 generates the fixed wavelength light (optical frequency $f_2$). It should be noted that the optical frequency $f_1$ changes from $f_2+\Delta f_{low}$ to $f_2+\Delta f_{high}$.

The demultiplexer 14 then receives the variable wavelength light from the variable wavelength light source 12, demultiplexes the variable wavelength light, and outputs the demultiplexed light to the first multiplexer 16 and the second multiplexer 26. Moreover, the demultiplexer 24 receives the fixed wavelength light from the fixed wavelength light source 22, demultiplexes the fixed wavelength light, and outputs the demultiplexed light to the first multiplexer 16 and the optical frequency converter 25. It should be noted that the difference frequency signal having the difference frequency $f_{IF}$ is also fed from the difference frequency signal source 30 to the optical frequency converter 25.

The first multiplexer 16 multiplexes the variable wavelength light and the fixed wavelength light with each other. The first terahertz light generator 18 receives the output from the first multiplexer 16, and outputs the incident light having the optical frequency $f_1-f_2$, which is the difference between the optical frequency $f_1$ of the variable wavelength light and the optical frequency $f_2$ of the fixed wavelength light.

The incident light is demultiplexed by the demultiplexer 46a, and is fed to the optical fiber 2 and the reference multiplexer 46c. The incident light fed to the optical fiber 2 transmits through the optical fiber 2, and emerges from the other end of the optical fiber 2 as the response light. The response light is fed to the third multiplexer 42.

The optical frequency converter 25 converts the optical frequency $f_2$ of the fixed wavelength light by the amount of the difference frequency $f_{IF}$, and outputs the converted light. The light (optical frequency $f_2+f_{IF}$) output from the optical frequency converter 25 is fed to the second multiplexer 26.

The second multiplexer 26 multiplexes the variable wavelength light and the light output by the optical frequency converter 25 with each other. The second terahertz light generator (second light output means) 28 receives the output from the second multiplexer 26, and outputs the reference light having the optical frequency $f_1-f_2-f_{IF}$, which is the difference between the optical frequency $f_1$ of the variable wavelength light and the optical frequency $f_2+f_{IF}$ of the light output by the optical frequency converter 25.

The reference light is demultiplexed by the demultiplexer 46b, and is fed to the third multiplexer 42 and the reference multiplexer 46c.

The third multiplexer 42 multiplexes the response light and the reference light with each other, and feeds the multiplexed light to the terahertz light detector 44. The terahertz light detector 44 receives the output from the third multiplexer 42, and outputs the light detection signal having the frequency $f_{IF}$ (namely, the difference frequency $f_{IF}$) which is the difference between the optical frequency $f_1-f_2$ of the response light and the optical frequency $f_1-f_2-f_{IF}$ of the reference light.

The reference multiplexer 46c multiplexes the incident light and the reference light with each other, and feeds the multiplexed light to the terahertz light detector 44c. The terahertz light detector 44c receives the output from the reference multiplexer 46c, and outputs the reference signal having the frequency $f_{IF}$ (namely, the difference frequency $f_{IF}$) which is the difference between the optical frequency $f_1-f_2$ of the incident light and the optical frequency $f_1-f_2-f_{IF}$ of the reference light.

The network analyzer 50 receives the light detection signal from the terahertz light detector 44, and the reference signal from the terahertz light detector 44c, thereby measuring the characteristics of the optical fiber 2. Specifically, the amplitude/phase comparator 52 compares the amplitude (phase) of the light detection signal and the amplitude (phase) of the reference signal with each other. The data processing unit 54 carries out the data processing based on the result of the comparison, thereby measuring the amplitude characteristic and the phase characteristic of the optical fiber 2 within the range of the optical frequency of the incident light from $\Delta f_{low}$ to $\Delta f_{high}$.

According to the fourth embodiment, there are obtained the same effects as in the first embodiment. Moreover, according to the fourth embodiment, in place of the difference frequency signal, the reference signal, which is obtained by multiplexing the incident light and the reference light with each other, and then detecting the multiplexed light by the heterodyne detection on the terahertz optical detector 44c, is fed to the network analyzer 50. As a result, it is possible to resolve the instability of the transmission characteristics of the optical fiber 2.

According to the fourth embodiment, the characteristics of the optical fiber 2 are measured while the light which has transmitted through the optical fiber (device under test) 2 is considered as the response light. However, the light reflected by the optical fiber 2 may be considered as the response light as in the second embodiment. Moreover, both the light which has transmitted through the optical fiber 2 and the light which has reflected by the optical fiber 2 may be considered as the response light as in the third embodiment.

A computer is provided with a CPU, a hard disk, and a media (such as a floppy disk (registered trade mark) and a CD-ROM) reader, and the media reader is caused to read a medium recording a program realizing the above-described respective components (such as the amplitude/phase comparator 52 and the data processing unit 54), thereby installing the program on the hard disk. This method may also realize the above-described embodiment.

The invention claimed is:

1. A measuring device comprising:
   an incident light generator that generates incident light;
   a reference light generator that generates reference light which has an optical frequency different from the optical frequency of the incident light by a constant difference frequency;
   a light detection signal outputter that outputs a light detection signal having the difference frequency, based on response light obtained by making the incident light incident to a device under test, and the reference light;
   a characteristic measurer that receives the light detection signal, thereby measuring a characteristic of the device under test; and
   a difference frequency signal outputter that outputs a difference frequency signal having the difference frequency,
   wherein said incident light generator comprises:
      a variable wavelength light source that generates variable wavelength light;
      a fixed wavelength light source that generates fixed wavelength light;
      a first multiplexer that multiplexes the variable wavelength light and the fixed wavelength light with each other; and
      a first light outputter that receives an output from said first multiplexer, and outputs the incident light which has an optical frequency corresponding to a difference between the optical frequency of the variable wavelength light and the optical frequency of the fixed wavelength light, and
   said reference light generator comprises:
      said variable wavelength light source;
      said fixed wavelength light source;
      an optical frequency converter that receives the difference frequency signal and the fixed wavelength light, and converts the optical frequency of the fixed wavelength light by the amount of the difference frequency;
      a second multiplexer that multiplexes the variable wavelength light and an output from said optical frequency converter with each other; and
      a second light outputter that receives an output from said second multiplexer, and outputs the reference light.

2. The measuring device according to claim 1, wherein said characteristic measurer receives the difference frequency signal and the light detection signal, and measures the characteristic of the device under test.

3. A measuring device according to claim 1, comprising:
   a base multiplexer that multiplexes the incident light and the reference light with each other; and
   a reference signal outputter that receives an output from said base multiplexer, and outputs a reference signal having the difference frequency, wherein said characteristic measurer receives the reference signal and the light detection signal, and measures the characteristic of the device under test.

4. The measuring device according to claim 1, wherein the response light is light obtained by causing the incident light to transmit through the device under test.

5. The measuring device according to claim 1, wherein the response light is light obtained by causing the incident light to be reflected by the device under test.

6. A measuring device according to claim 4, comprising:
a base multiplexer that multiplexes the incident light and the reference light with each other; and
a reference signal outputter that receives an output from said base multiplexer, and outputs a reference signal having the difference frequency,
wherein said characteristic measurer receives the reference signal and the light detection signal, and measures the characteristic of the device under test.

7. A measuring device according to claim 5, comprising:
a base multiplexer that multiplexes the incident light and the reference light with each other; and
a reference signal outputter that receives an output from said base multiplexer, and outputs a reference signal having the difference frequency,
wherein said characteristic measurer receives the reference signal and the light detection signal, and measures the characteristic of the device under test.

8. A measuring method comprising:
generating variable wavelength light;
generating fixed wavelength light;
multiplexing the variable wavelength light and the fixed wavelength light with each other;
generating incident light from the multiplexed variable wavelength light and fixed wavelength light, the incident light having an optical frequency corresponding to a difference between an optical frequency of the variable wavelength light and an optical frequency of the fixed wavelength light;
outputting a difference frequency signal having a constant difference frequency;
receiving the difference frequency signal and the fixed wavelength light;
converting the optical frequency of the fixed wavelength light by the amount of the difference frequency;
multiplexing the variable wavelength light and the converted fixed wavelength light;
generating reference light from the multiplexed variable wavelength light and converted fixed wavelength light, the reference light having an optical frequency different from the optical frequency of the incident light by constant difference frequency;
outputting a light detection signal having the difference frequency, based on response light obtained by making the incident light incident to a device under test, and the reference light; and
receiving the light detection signal, thereby measuring a characteristic of the device under test.

* * * * *

UNITED STATES PATENT AND TRADEMARK OFFICE
CERTIFICATE OF CORRECTION

| | | |
|---|---|---|
| PATENT NO. | : 7,697,122 B2 | Page 1 of 1 |
| APPLICATION NO. | : 12/065658 | |
| DATED | : April 13, 2010 | |
| INVENTOR(S) | : T. Yamashita et al. | |

It is certified that error appears in the above-identified patent and that said Letters Patent is hereby corrected as shown below:

Column 16, line 21 (claim 8, line 23) of the printed patent, insert -- the -- after "by".

Signed and Sealed this

Nineteenth Day of October, 2010

David J. Kappos
*Director of the United States Patent and Trademark Office*